United States Patent [19]

Manami et al.

[11] Patent Number: 4,778,932

[45] Date of Patent: Oct. 18, 1988

[54] PROCESS FOR PREPARING DIARYLSULFONES

[75] Inventors: Hiroshi Manami, Jyoyo; Shigeo Miki, Hirakata; Mikio Nakazawa, Uji, all of Japan

[73] Assignee: New Japan Chemical Co., Ltd., Kyoto, Japan

[21] Appl. No.: 70,576

[22] Filed: Jul. 7, 1987

[30] Foreign Application Priority Data

Jul. 16, 1986 [JP] Japan ............................ 61-168579
Sep. 9, 1986 [JP] Japan ............................ 61-213368
Sep. 3, 1987 [JP] Japan ............................ 62-53740

[51] Int. Cl.$^4$ .................................... C07C 147/10
[52] U.S. Cl. .................................... 568/33; 564/430; 568/30; 568/32; 568/34
[58] Field of Search ................ 568/30, 33, 34; 564/430

[56] References Cited

U.S. PATENT DOCUMENTS

| 3,501,532 | 3/1970 | Minor et al. | 568/34 |
| 3,729,517 | 4/1973 | Bracke | 260/505 A |
| 4,089,904 | 5/1978 | Cisney et al. | 568/37 |

*Primary Examiner*—Mary E. Ceperley
*Attorney, Agent, or Firm*—Larson and Taylor

[57] ABSTRACT

In preparing a diarylsulfone by condensing sulfuric acid or an aromatic sulfonic acid with an aromatic compound having at least one replaceable hydrogen atom on the aromatic ring, the process of the present invention is characterized in that the condensation reaction is carried out in the presence of at least one catalyst selected from the group consisting of a tungstic acid, molybdic acid and heteropoly acid thereof.

18 Claims, No Drawings

PROCESS FOR PREPARING DIARYLSULFONES

The present invention relates to a process for preparing a diarylsulfone from sulfuric acid or an aromatic sulfonic acid and an aromatic compound.

The diarylsulfones prepared according to the present invention are useful compounds as materials or intermediates for synthesizing heat-resistant resins such as polyesters, polyamides, polyimides, polysulfones or the like.

A variety of processes as given below have been proposed for preparing diarylsulfones.

(1) A process in which an aromatic sulfochloride and an aromatic compound are subjected to Friedel-Crafts reaction in the presence of a Lewis acid catalyst such as anhydrous aluminum chloride, anhydrous ferric chloride or the like (e.g., German patent No. 701954).

(2) A process in which an aromatic sulfochloride is reacted with an aromatic compound in the presence of an aromatic sulfonic acid (e.g., Japanese Examined patent Publication No. 5707/1975).

(3) A process in which an aromatic sulfochloride is reacted with an aromatic compound in the presence of a sulfone-type ion-exchange resin or excessively acidic resin (Japanese Examined patent Publication No. 53345/1975 and Japanese Unexamined patent Publication No. 81453/1982).

However, these three processes have the drawback that the aromatic sulfochloride used as the starting material is prone to hydrolysis in handling or during storage.

In view of this shortcoming, it was thought industrially advantageous to prepare diarylsulfones by a process in which sulfuric acid or an aromatic sulfonic acid which are both stable and easy to handle is reacted directly with an aromatic compound. From this viewpoint, the following processes have been proposed.

(4) A process in which a benzene compound is reacted with a mixture of sulfuric anhydride and dimethyl sulfate (methyl pyrosulfate) (e.g., British patent No. 895464 and Japanese Examined patent Publication No. 11817/1962).

(5) A process in which an arylsulfonic acid is synthesized from a benzene compound and sulfuric acid and the resulting arylsulfonic acid is reacted with a benzene compound in the presence or the absence of a dehydrating agent such as $P_2O_5$ or the like (U.S. Pat. No. 3729517 and Japanese Unexamined patent Publication No. 92256/1985).

(6) A process in which an aromatic sulfonic acid and an aromatic compound are subjected to condensation reaction at a high temperature under a high pressure (Japanese Unexamined patent Publication No. 76834/1974).

(7) A process in which an aromatic sulfonic acid is reacted with an aromatic compound in the presence of an excessively acidic resin (Japanese Unexamined patent Publication No. 85363/1982).

These processes, however, have drawbacks. Stated more specifically, the process (4) uses a large amount of highly toxic dimethyl sulfate, requiring consideration of equipment to cope with the problems of operators' hygienic conditions and disposal of waste oils. The process (5) gives a final product in low yields when performed in the absence of dehydrating agent and needs to use a large amount of expensive dehydrating agent to increase the yield. The process (6) produces the contemplated sulfones in low yields along with great quantities of isomers as by-products and requires a high-pressure reactor. The process (7) uses a large amount of excessively acidic resin which is expensive.

It is an object of the present invention to provide a process for preparing a high-purity diarylsulfone in a high yield from an aromatic compound and sulfuric acid or an aromatic sulfonic acid which is easy to handle and cheaply available.

Other objects and features of the present invention will become apparent from the following description.

In preparing a diarylsulfone by condensing sulfuric acid or an aromatic sulfonic acid with an aromatic compound having at least one replaceable hydrogen atom on the aromatic ring, the process of the present invention is characterized in that the condensation reaction is carried out in the presence of at least one catalyst selected from the group consisting of tungstic acid, molybdic acid and a heteropoly acid thereof.

Our research has revealed that when tungstic acid, molybdic acid or a heteropoly acid thereof is present in the reaction system for the preparation of a diarylsulfone by reacting sulfuric acid or an aromatic sulfonic acid with an aromatic compound, the tungstic acid, molybdic acid or heteropoly acid thereof exhibits a significantly high catalytic activity so that the desired high-purity diarylsulfone can be produced in high yields.

Aromatic compounds useful as one of the starting compounds in the invention include a variety of those having 1 to 3 replaceable hydrogen atoms on the aromatic ring and conventionally used for this type of reactions.

Typical examples of useful aromatic compounds are benzene compounds and naphthalene compounds represented by the formula

$Ar-(R^1)_m$ wherein Ar is benzene or naphthalene ring, $R^1$ is an alkyl group having 1 to 20 carbon atoms, substituted alkyl group having 1 to 20 carbon atoms, phenyl group, hydroxyl group, halogen atom, amino group, nitro group, alkoxy group having 1 to 20 carbon atoms, phenoxy group or substituted phenoxy group, and m is 0 or an integer of 1 to 3. Exemplary of substituents for substituted alkyl groups are a hydroxy group, halogen atom and the like. Representative of substituents for substituted phenoxy groups are an alkyl group having 1 to 20 carbon atoms, hydroxyl group, halogen atom, amino group, nitro group, alkoxy group having 1 to 20 carbon atoms and the like.

Among these substituents represented by $R^1$, preferable is an alkyl group, halogen atom, etc., and more preferable is an alkyl group having 1 to 12 carbon atoms. Illustrative of representative aromatic compounds are benzene, toluene, ethylbenzene, propylbenzene, butylbenzene, dodecylbenzene, phenol, biphenyl, fluorobenzene, chlorobenzene, bromobenzene, iodobenzene, nitrobenzene, aniline, anisole, biphenyl ether, benzophenone, xylene, dichlorobenzene, dibromobenzene, ethylmethylbenzene, chloroethylbenzene, bromoethylbenzene, chlorotoluene, bromotoluene, nitrotoluene, trimethylbenzene, trichlorobenzene, tribromobenzene, β-chloroethylbenzene, β-bromoethylbenzene, β-iodoethylbenzene, nitrophenol, toluidine, catechol, resorcin, hydroquinone, chlorophenol, bromophenol, xylenol, naphthalene, methylnaphthalene, naphthol, etc.

Sulfuric acid or an aromatic sulfonic acid is used as the other starting material in the invention. These acids are easy to handle and inexpensive to obtain in large amounts. Usable as aromatic sulfonic acids are those conventionally used for this type of reactions. Typical examples thereof are benzenesulfonic acid, naphthalenesulfonic acid, nucleus-substituted benzenesulfonic acid and nucleus-substituted naphthalenesulfonic acid which are all represented by the formula $(R^2)_n-Ar-SO_3H$ wherein Ar is benzene or naphthalene ring, $R^2$ is an alkyl group having 1 to 20 carbon atoms, substituted alkyl group having 1 to 20 carbon atoms, phenyl group, hydroxy group, halogen atom, amino group, nitro group, alkoxy group having 1 to 20 carbon atoms, phenoxy group or substituted phenoxy group, and n is 0 or an integer of 1 to 3. Exemplary of substituents for substituted alkyl groups are a hydroxy group, halogen atom and the like. Illustrative of substituents for substituted phenoxy groups are an alkyl group having 1 to 20 carbon atoms, hydroxy group, halogen atom, amino group, nitro group, alkoxy group having 1 to 20 carbon atoms and the like.

Examples of aromatic sulfonic acids are benzenesulfonic acid, toluenesulfonic acid, ethylbenzenesulfonic acid, β-chloroethylbenzenesulfonic acid, β-bromoethylbenzenesulfonic acid, β-iodoethylbenzenesulfonic acid, dodecylbenzenesulfonic acid, hydroxybenzenesulfonic acid, phenylbenzenesulfonic acid, fluorobenzenesulfonic acid, chlorobenzenesulfonic acid, bromobenzenesulfonic acid, iodobenzenesulfonic acid, nitrobenzenesulfonic acid, methoxybenzenesulfonic acid, phenoxybenzenesulfonic acid, xylenesulfonic acid, dichlorobenzenesulfonic acid, dibromobenzenesulfonic acid, trimethylbenzenesulfonic acid, naphthalenesulfonic acid, methylnaphthalenesulfonic acid, hydroxynaphthalenesulfonic acid, etc.

Examples of catalysts useful in this invention are tungstic acid, molybdic acid and heteropoly acids thereof. The term "heteropoly acid" used herein refers to a polyacid formed from at least two oxyacids. Useful poly acid atoms are tungsten and molybdenum. Usable hetero-atoms are various as exemplified below. Examples of heteroatoms in heteropoly acids of tungstic acid are P, As, Si, Ti, Co, Fe, B, V, Be, I, Ni, Ga, etc. Examples of heteropoly acids of tungstic acid are those having the formulas: $H_3[PW_{12}O_{40}]$, $H_3[AsW_{12}O_{40}]$, $H_4[SiW_{12}O_{40}]$, $H_4[TiW_{12}O_{40}]$, $H_5[CoW_{12}O_{40}]$, $H_5[FeW_{12}O_{40}]$, $H_5[BW_{12}O_{40}]$, $H_3[VW_{12}O_{40}]$, $H_6[BeW_9O_{31}]$, $H_6[TeW_6O_{24}]$, $H_5[IW_6O_{24}]$, $H_4[NiW_6O_{24}H_6]$, $H_3[GaW_6O_{24}H_6]$, $H_6[P_2W_{18}O_{62}]$, $H_6[As_2W_{18}O_{62}]$, $H_7[PW_{11}O_{33}]$, etc. Examples of hetero-atoms in heteropoly acids of molybdic acid are P, As, Si, Ge, Ti, Ce, Th, Mn, Ni, Te, I, Co, Cr, Fe, Ga, etc. Examples of heteropoly acids of molybdic acid are those represented by the formulas: $H_3[PMo_{12}O_{40}]$, $H_3[AsMo_{12}O_{40}]$, $H_4[SiMo_{12}O_{40}]$, $H_4[GeMo_{12}O_{40}]$, $H_4[TiMo_{12}O_{40}]$, $H_8[CeMo_{12}O_{42}]$, $H_8[ThMo_{12}O_{42}]$, $H_7[PMo_{11}O_{39}]$, $H_7[AsMo_{11}O_{39}]$, $H_8[GeMo_{11}O_{39}]$, $H_6[MnMo_9O_{32}]$, $H_6[NiMo_9O_{32}]$, $H_6[TeMo_6O_{24}]$, $H_5[IMo_6O_{24}]$, $H_3[CoMo_6O_{24}H_6]$, $H_3[CrMo_6O_{24}H_6]$, $H_3[FeMo_6O_{24}H_6]$, $H_3[GaMo_6O_{24}H_6]$, $H_4[NiMo_6O_{24}H_6]$, $H_6[P_2Mo_{18}O_{62}]$, $H_6[AsMo_{18}O_{62}]$, etc. Also usable are mixed coordination heteropoly acids such as tungstomolybdo-phosphoric acid, tungstovanadophosphoric acid, vanadomolybdophosphoric acid, tungstomolybdosilicic acid, tungstovanadosilicic acid, vanadomolybdosilicic acid, etc. Examples thereof are $H_4PMoW_{11}O_{40}$, $H_4PReW_{11}O_{40}$, $H_4PVMo_{11}O_{40}$, $H_5PV_2Mo_{10}O_{40}$, $H_3PMo_6W_6O_{40}$, etc. The heteropoly acids exemplified above are known compounds. Heteropoly acids containing P or Si as the hetero-atom are preferred because of the ease of preparation or availability. Of such heteropoly acids, 12-tungstophosphoric acid ($H_3PW_{12}O_{40}$), 12-tungstosilicic acid ($H_3SiW_{12}O_{40}$), 12-molybdophosphoric acid ($H_3PMo_{12}O_{40}$) and the like are more preferred.

The tungstic acid, molybdic acid and heteropoly acids thereof to be used as the catalyst in this invention may be employed in the form of a hydrate or in the form of a compound capable of forming the foregoing tungstic acid, molybdic acid or heteropoly acids thereof in the reaction system. Examples of such compounds are salts of alkali metals such as potassium, sodium and the like; salts of heavy metals such as cobalt, nickel, manganese, copper and the like; salts of ammonium ($NH_4$), etc. The tungstic acid and molybdic acid may be used also in the form of oxides, chlorides and sulfides represented by $MO_3$, $MCl_6$ and $MS_3$ (wherein M=W or Mo), respectively. When the foregoing salts, oxides, chlorides or sulfides are used, it is preferable to incorporate a mineral acid such as phosphoric acid, hydrochloric acid, sulfuric acid or the like into the reaction system to adjust the pH to 4 or less so that the reaction is carried out under such acidic conditions.

The catalysts given above are usable singly or at least two of them can be used in admixture.

Heteropoly acids are desirable in terms of the reactivity while tungstic acid is desired in consideration of the balance between the reactivity and the costs.

The catalysts used can be easily recovered and repeatedly reused without special treatment.

The process of the present invention for preparing a diarylsulfone is usually carried out in the following manner.

Sulfuric acid or aromatic sulfonic acid, part or the whole of predetermined amount of aromatic compound and a catalyst are placed into a reactor and subjected to reaction at a temperature of about 60° to about 280° C. while removing the water produced. When the aromatic compound is charged into the reactor in part of the predetermined amount at the start of the reaction, the remaining part thereof is fed during the process of reaction while maintaining the system at the reaction temperature.

The water produced by the reaction can be removed, for example, by phase separation of the azeotropic mixture with the aromatic compound which is refluxed to the reaction system, by introducing a nitrogen gas or like carrier gas into the reaction mixture, or by conducting the reaction under a reduced pressure.

It is preferred to use the aromatic compound in a stoichiometric or excessive amount relative to the sulfuric acid or aromatic sulfonic acid, usually in an amount of about 2 to about 10 moles per mole of the sulfuric acid and about 1 to about 20 moles per mole of the aromatic sulfonic acid. Less than stoichiometric amount of the aromatic compound used tends to reduce the yield of diarylsulfone produced, whereas a larger amount of the aromatic compound used provides nothing advantageous, hence uneconomical.

The amount of the catalyst to be used can be widely varied insofar as the amount is effective for exhibiting the catalytic activity. Yet from viewpoints of reaction rate and economy, it is advantageous to use the catalyst in an amount of about 0.01 to about 30% by weight, preferably about 0.1 to about 15% by weight, based on the sulfuric acid or aromatic sulfonic acid.

The reaction is performed at a temperature of between about 60° C. and about 280° C., preferably about 100° C. and about 230° C., although it is variable depending on the kinds of aromatic sulfonic acid and aromatic compound, the desired reaction time and other conditions. A proper reaction rate is difficult to determine at a reaction temperature of less than 60° C. while a side reaction such as polymerization or the like is likely to occur at a temperature of more than 280° C., resulting in production of a diarylsulfone in a lower yield.

The reaction period is usually within 1 to 50 hours, although it may vary over a wide range depending on the reaction conditions such as the amount of catalyst used, kind of aromatic compound and aromatic sulfonic acid used, reaction temperature, etc.

In practicing the present invention, a dehydrating agent, preferably phosphorus oxide and/or condensed phosphoric acid, may be incorporated into the reaction system to increase the yield of the contemplated final product and to shorten the reaction time. Our research revealed that if the dehydrating agent is added after the progress of the reaction to a certain stage instead at the start thereof, a noticeably smaller amount of dehydrating agent used can produce the desired effect than when the agent is added at the start thereof. This mode of addition is not only economical but also able to decrease the content of phosphoric acid in waste water, facilitating disposal of waste water. It is suitable that the dehydrating agent be added when the conversion of aromatic sulfonic acid has reached about 40 to about 95%, preferably about 70 to about 95%. In other words, the dehydrating agent is preferably added to the reaction system when the conversion of aromatic sulfonic acid has come to the value in said range. When sulfuric acid is used in place of aromatic sulfonic acid, the dehydrating agent can be added at the above conversion (40 to 95%, preferably 70 to 95%) of aromatic sulfonic acid, as the sulfuric acid is intermediately converted to aromatic sulfonic acid which is turned into the desired diarylsulfone. Earlier addition of dehydrating agent fails to give a satisfactory effect as contemplated unless a greater amount thereof is added. Nor later addition thereof produces a fully satisfactory effect.

When an aromatic compound free of alkyl substituent on the aromatic ring such as benzene, chlorobenzene or the like is used as the starting compound, the reaction may take a relatively long period of time to complete. The dehydrating agent can be effectively used to remedy the problem thus arisen.

Usable as the dehydrating agent are phosphorus oxides and condensed phosphoric acids heretofore used for this kind of reactions. Examples of phosphorus oxides useful in the invention are phosphorus pentoxide, diphosphorus trioxide, etc. Useful condensed phosphoric acids include metaphosphoric acid, pyrophosphoric acid, tripolyphosphoric acid, trimetaphosphoric acid, tetrametaphosphoric acid and the like.

Preferred amount of the phosphorus dehydrating agent to be used in the process of this invention is about 0.01 to about 1.0 mole, preferably about 0.025 to about 0.5 mole, calculated as phosphoric acid, per mole of the aromatic sulfonic acid or sulfuric acid used as the starting material. A lesser content of phosphorus compound tends to give little effect of increasing the yield of the contemplated product, whereas a higher content thereof increases the costs for the disposal of waste water, hence economically disadvantageous.

Sulfonation is completed about 1 to 10 hours after the addition of phosphorus dehydrating agent.

When required, the reaction mixture thus obtained is diluted with an aromatic compound to be used as the starting material for the reaction or with an organic solvent such as lower alcohol, ether, ketone or the like, then the catalyst is separated by filtration and the mother liquor is cooled to deposit the crystals or the diluting medium is removed from the mother liquor by distillation, whereby a diarylsulfone is obtained. Water washing, if required, may be performed in any step of the foregoing procedure. The recovered catalyst and diluting medium can be reused as they are.

A higher-purity diarylsulfone can be produced by recrystallization of the reaction mixture from methanol, ethanol or like aliphatic lower alcohol or toluene, xylene or like aromatic compound.

The present invention will be described below in more detail with reference to the following examples and comparison examples.

EXAMPLE 1

Into reactor placed 130 (1.2 moles) of o-xylene, 100 g (1.0 mole) of 98% sulfuric acid and 10 g of 12-tungstophosphoric acid ($H_3PW_{12}O_{40}$.hydrate). The reaction temperature was raised to the reflux temperature while the mixture was stirred. The reaction system was kept at the reflux temperature for 0.5 hour, while refluxing the o-xylene and removing the produced water by subjecting the azeotropic mixture with the o-xylene to phase separation. A 130 g (1.2 moles) quantity of o-xylene was further added dropwise to the reaction system, which was maintained at the reflux temperature for 4.5 hours while distilling off the water produced. The amount of water distilled off during the reaction was 39 ml which corresponded to the stoichiometric amount. The reaction mixture was diluted with 260 g of o-xylene and the catalyst was separated by filtration. The residue was cooled and the precipitate was filtered, followed by washing with water and drying, giving 266 g of tetramethyldiphenylsulfone in a yield of 97%. The reaction product thus obtained was subjected to gas chromatography for analysis, which showed that the ratio of 3,3',4,4'-tetramethyldiphenylsulfone to the other isomers was 99.3:0.7.

EXAMPLE 2

The general procedure of Example 1 was repeated with the exception of using 5.0 g of tungstic acid as a catalyst. The amount of water distilled off during 5 hours of reaction was 36 ml which means that the reaction produced water in an amount corresponding to 94% of stoichiometric amount. The reaction mixture was treated in the same manner as in Example 1, producing 248 g of tetramethyldiphenylsulfone (90% yield), which was analyzed by gas chromatography. The ratio of 3,3',4,4'-tetramethyldiphenylsulfone to the other isomers was 94.5:5.5.

COMPARISON EXAMPLE 1

The same reaction as in Example 1 was effected in the absence of a catalyst. Only 28 ml of water was distilled off even by 12 hours of reaction. The same treatment of the reaction mixture as in Example 1 gave 143 g of tetramethyldiphenylsulfone (yield 52%), which was analyzed to find that the ratio of 3,3',4,4'-tetramethyldiphenylsulfone to the other isomers was 88.2:11.8.

EXAMPLE 3

Into a reactor were placed 112 g (1.2 moles) of toluene, 100 g (1.0 mole) of 98% sulfuric acid and 5 g of 12-tungstosilicic acid ($H_4SiW_{12}O_{40}.24H_2O$) The reaction temperature was elevated to the reflux temperature while stirring the mixture. The reaction system was kept at the reflux temperature for 1 hour, while refluxing the toluene and removing the produced water by subjecting the azeotropic mixture with the toluene to phase separation. Maintaining the reflux temperature, 112 g (1.2 moles) of toluene was further added dropwise and the mixture underwent 7 hours of reaction while distilling off the water produced. The reaction mixture was diluted with 224 g of toluene and the catalyst was separated by filtration. After the residue was cooled, the precipitate was filtered, washed with water and dried, giving 241 g of dimethyldiphenylsulfone (98% yield). Analysis of the product by gas chromatography showed that the ratio of 4,4'-dimethyldiphenylsulfone to the other isomers was 96.3:3.7.

COMPARISON EXAMPLE 2

The same reaction as in Example 3 was carried out for 8 hours without a catalyst. The reaction mixture was treated in the same manner as in Example 3, giving 62 g of dimethyldiphenylsulfone (25% yield), which was analyzed to find that the ratio of 4,4'-dimethyldiphenylsulfone to the other isomers was 89.2:10.8. The reaction product was obtained with a purity of 89.2% in a yield of 25%, namely without favorable results in these respects.

EXAMPLE 4

Into a reactor were placed 248 g (2.2 moles) of chlorobenzene, 100 g (1.0 mole) of 98% sulfuric acid and 5 g of 12-tungstophosphoric acid. While stirring the mixture, the reaction temperature was raised to the reflux temperature. The reaction system was kept at the reflux temperature for 10 hours, while refluxing the chlorobenzene and removing the produced water by subjecting the azeotropic mixture with the chlorobenzene to phase separation. The reaction mixture was diluted with 100 g of chlorobenzene and the catalyst was separated by filtration. After addition of water to the mother liquor, the mixture was thoroughly stirred and the aqueous layer was separated. The chlorobenzene was removed from the organic layer by distillation under reduced pressure, giving 260 g of dichlorodiphenylsulfone (91% yield). The reaction product thus obtained was analyzed by gas chromatography, which showed that the ratio of 4,4'-dichlorodiphenylsulfone to the other isomers was 93.2:6.8.

COMPARISON EXAMPLE 3

The same reaction as in Example 4 was effected for 10 hours without a catalyst. The reaction mixture was treated in the same manner as in Example 4, giving 52 g of dichlorodiphenylsulfone (18% yield). The reaction product thus obtained was analyzed, which showed that the ratio of 4,4'-dichlorodiphenylsulfone to the other isomers was 85.3:14.7.

EXAMPLE 5

Into a reactor were placed 368 g (2.5 moles) of o-dichlorobenzene, 100 g (1.0 mole) of 98% sulfuric acid and 10 g of molybdic acid. The mixture was subjected to the same reaction as in Example 4 for 20 hours, giving 271 g of tetrachlorodiphenylsulfone (76% yield). The ratio of 3,3',4,4'-tetrachlorodiphenylsulfone to the other isomers was 89.2:10.8.

EXAMPLE 6

Into a reactor were placed 288 g (3.0 moles) of phenol, 100 g (1.0 mole) of 98% sulfuric acid and 5 g of 12-tungstophosphoric acid. The mixture was heated with agitation. The reaction system was kept at the reflux temperature for 2 hours, while refluxing the phenol and removing the produced water by subjecting the azeotropic mixture with the phenol to phase separation. Thereafter 100 g of phenol was further added and the catalyst was separated by filtration. The mother liquor was washed with water and the phenol was distilled off under reduced pressure, giving 240 g of dihydroxydiphenyl-sulfone (96% yield). Analysis of the product showed that the ratio of 4,4'-dihydroxydiphenylsulfone to the other isomers was 97.4:2.6.

COMPARISON EXAMPLE 4

The same reaction as in Example 6 was performed without a catalyst. The reaction mixture resulting from 2 hours of reaction was treated in the same manner as in Example 6, giving 124 g of dihydroxydiphenylsulfone (50% yield), which was analyzed to find that the ratio of 4,4'-dihydroxydiphenylsulfone to the other isomers was 91.3:8.7.

EXAMPLE 7

The same reaction as in Example 1 was repeated with the exception of using, as a catalyst, a 9.8 g portion of 12-tungstophosphoric acid recovered in Example 1, producing 260 g of tetramethyldiphenylsulfone (95% yield) which was found to be 98.9:1.1 in the ratio of 3,3',4,4'-tetramethyldiphenylsulfone to the other isomers.

EXAMPLE 8

A 158 g (1.0 mole) quantity of benzenesulfonic acid, 94 g (1.2 moles) of benzene and 5 g of 12-tungstophosphoric acid ($H_3PW_{12}O_{40}.29H_2O$) were refluxed with heating and stirring. The reaction system was kept at the reflux temperature for 10 hours, while refluxing the benzene and removing the produced water by subjecting the azeotropic mixture with the benzene to phase separation. The reaction mixture was diluted with 150 g of benzene and the catalyst was separated by filtration. The mother liquor was washed with water and the benzene was distilled off under reduced pressure, giving 210 g of diphenylsulfone (96% yield, m.p. 124° to 128° C.).

EXAMPLE 9

The same reaction as in Example 1 was performed for 15 hours using 190 g (1.0 mole) of p-toluenesulfonic acid.monohydrate, 111 g (1.2 moles) of toluene and a 4.5 g portion of the catalyst recovered in Example 1. After completion of the reaction, the reaction mixture was diluted with 200 g of toluene and the catalyst was separated by filtration. After the mother liquor was cooled, the precipitate was filtered, washed with water and dried, giving 231 g of dimethyldiphenylsulfone in a yield of 94% (melting point 153° to 156° C.).

COMPARISON EXAMPLE 5

The same reaction as in Example 9 was conducted for 15 hours without a catalyst, producing 27 g of dimethyldiphenylsulfone in a yield of 11% (melting point 154° to 156° C.).

EXAMPLE 10

A 193 g (1.0 mole) quantity of p-chlorobenzenesulfonic acid, 169 g (1.5 moles) of chlorobenzene and 10 g of 12-tungstosilicic acid ($H_4SiW_{12}O_{40}.24H_2O$) were refluxed with heating and stirring. The reaction system was kept at the reflux temperature for 20 hours, while refluxing the chlorobenzene and removing the produced water by subjecting the azeotropic mixture with the chlorobenzene to phase separation. The reaction mixture was cooled and the catalyst was separated by filtration. After the mother liquor was washed with water, the chlorobenzene was distilled off under reduced pressure, giving 267 g of dichlorodiphenylsulfone in a yield of 93% (melting point 145° to 148° C.).

EXAMPLE 11

A 222 g (1.0 mole) quantity of o-xylene-4sulfonic acid.dihydrate and 10 g of 12-tungstophosphoric acid were heated with stirring to 150° to 180° C. A 127 g (1.2 moles) quantity of o-xylene was added dropwise. An azeotropic mixture of the water produced and o-xylene were cooled and subjected to phase separation to remove the water and to reflux the o-xylene. After 5 hours of reaction, the reaction mixture was diluted with 300 g of o-xylene and the catalyst was separated by filtration. After the mother liquor was cooled, the precipitate was filtered, washed with water and dried, giving 266 g of tetramethyldiphenylsulfone in a yield of 97% (melting point 163° to 165° C.). The reaction product thus obtained was recrystallized from xylene, producing a high-purity 3,3',4,4'-tetramethyldiphenylsulfone (melting point 164° to 165° C.).

COMPARISON EXAMPLE 6

The same reaction as in Example 11 was performed for 12 hours without a catalyst. The reaction mixture was treated in the same manner as in Example 11, giving 151 g of tetramethyldiphenylsulfone in a yield of 55% (melting point 160° to 165° C.).

EXAMPLE 12

The same reaction as in Example 11 was repeated with the exception of using 5 g of tungstic acid ($H_2WO_4$) in place of 12-tungstophosphoric acid. The reaction mixture was treated in the same manner as in Example 11, giving 247 g of tetramethyldiphenylsulfone in a yield of 90% (melting point 161° to 164° C.).

EXAMPLE 13

A 193 g (1.0 mole) quantity of p-chlorobenzenesulfonic acid, 188 g (2.0 moles) of phenol and 10 g of 12-molybdophosphoric acid ($H_3PMol_{12}O_{40}$.hydrate) were refluxed with heating and stirring. An azeotropic mixture of the water formed and phenol were cooled and subjected to phase separation to reflux the phenol thus separated to the reaction system. After 6 hours of reaction, the reaction mixture was cooled and the catalyst was separated by filtration. After the mother liquor was washed with water, the phenol was distilled off under reduced pressure, giving 247 g of (4-chlorophenylsulfonyl)phenol in a yield of 92% (melting point 142° to 145° C.).

EXAMPLE 14

The same reaction as in Example 9 was performed for 10 hours using 190 g (1.0 mole) of p-toluenesulfonic acid.monohydrate, 127 g (1.2 moles) of o-xylene and 10 g of 12-tungstophosphoric acid. The reaction mixture was treated in the same manner as in Example 9, giving 247 g of trimethyldiphenylsulfone in a yield of 95% (melting point 128° to 131° C.).

EXAMPLE 15

A 158 g (1.0 mole) quantity of benzenesulfonic acid, 94 g (1.2 moles) of benzene and 5 g of 12-tungstophosphoric acid ($H_3PW_{12}O_{40}.29H_2O$) were refluxed with heating and stirring to undergo reaction for 4 hours. The reaction mixture was analyzed by high-performance liquid chromatography with the result that the benzenesulfonic acid had a conversion of 85%. To the reaction mixture was added 10 g of polyphosphoric acid (0.11 mole, calculated as phosphoric acid, per mole of benzenesulfonic acid). The mixture was refluxed for 2 hours. The reaction mixture was diluted with 200 g of benzene and was washed with water. The benzene was distilled off under reduced pressure, giving 210 g of diphenylsulfone in a yield of 96%.

EXAMPLE 16

A 100 g (1.0 mole) quantity of 98% sulfuric acid, 127 g (1.2 moles) of o-xylene and 5.0 g of 12-tungstosilicic acid ($H_4SiW_{12}O_{40}.24H_2O$) were refluxed with heating and stirring. Thereto was added dropwise 107 g (1.0 mole) of o-xylene. After 6 hours of reaction, the reaction mixture was analyzed by high-performance liquid chromatography, which revealed that the conversion of o-xylenesulfonic acid was 90%. To the reaction mixture was added 5.7 g (0.08 mole, calculated as phosphoric acid, per mole of sulfuric acid) of phosphorus pentoxide. The mixture was refluxed for 2 hours. The reaction mixture was diluted with 300 g of o-xylene and washed with water. The xylene was distilled off under reduced pressure, giving 263 g of 3,3'4,4'-tetramethyldiphenylsulfone in a yield of 96% (melting point 164° to 165° C.).

EXAMPLE 17

A 190 g (1.0 mole) quantity of p-toluenesulfonic acid.monohydrate, 127 g (1.2 moles) of o-xylene and 3 g of 12-tungstophosphoric acid ($H_3PW_{12}O_{40}.30H_2O$) were refluxed with heating and stirring to undergo 8 hours of reaction. The reaction mixture was analyzed by high-performance liquid chromatography, which showed that the conversion of p-toluenesulfonic acid was 82%. To the reaction mixture was added 10 g (0.14 mole, calculated as phosphoric acid, per mole of p-toluenesulfonic acid) of phosphorus pentoxide. The mixture was refluxed for 3 hours. The reaction mixture was diluted with 300 g of o-xylene and washed with water. The o-xylene was distilled off under reduced pressure, giving 247 g of 3,4,4'-trimethyldiphenylsulfone in a yield of 95% (melting point 128° to 131° C.).

COMPARISON EXAMPLE 7

A 158 g (1.0 mole) quantity of benzenesulfonic acid, 94 g (1.2 moles) of benzene and 5 g of 12-tungstophosphoric acid ($H_3PW_{12}O_{40}.29H_2O$) were refluxed with heating and stirring to undergo reaction for 30 minutes.

The reaction mixture was analyzed by highperformance liquid chromatography, which showed that the conversion of benzenesulfonic acid was 30%. To the reaction mixture was added the same amount (10 g) of polyphosphoric acid as in Example 15. The mixture was refluxed for 5.5 hours. The same treatment as in Example 15 was followed, giving 87 g of diphenylsulfone in a yield of 40%.

We claim:

1. In preparing a diarylsulfone by condensing sulfuric acid or an aromatic sulfonic acid with an aromatic compound having at least one replaceable hydrogen atom on the aromatic ring, a process which is characterized in that said condensation reaction is carried out in the presence of at least one catalyst selected from the group consisting of tungstic acid, molybdic acid and a heteropoly acid thereof.

2. A process according to claim 1 in which said aromatic compound is a compound represented by the formula $$Ar-(R^1)_m$$

wherein Ar is benzene or naphthalene ring, $R^1$ is an alkyl group having 1 to 20 carbon atoms, substituted alkyl group having 1 to 20 carbon atoms, phenyl group, hydroxy group, halogen atom, amino group, nitro group, alkoxy group having 1 to 20 carbon atoms, phenoxy group or substituted phenoxy group, and m is 0 or an integer of 1 to 3.

3. A process according to claim 1 in which said aromatic sulfonic acid is a compound represented by the formula $$(R^2)_n-Ar-SO_3H$$

wherein Ar is benzene or naphthalene ring, $R^2$ is an alkyl group having 1 to 20 carbon atoms, substituted alkyl group having 1 to 20 carbon atoms, phenyl group, hydroxy group, halogen atom, amino group, nitro group, alkoxy group having 1 to 20 carbon atoms, phenoxy group or substituted phenoxy group, and n is 0 or an integer of 1 to 3.

4. A process according to claim 1 in which said catalyst is tungstic acid.

5. A process according to claim 1 in which said catalyst is molybdic acid.

6. A process according to claim 1 in which said catalyst is a heteropoly acid of tungstic acid or molybdic acid.

7. A process according to claim 6 in which said heteropoly acid is a heteropoly acid of tungstic acid in which the hetero-atom is one selected from the group consisting of P, As, Si, Ti, Co, Fe, B, V, Be, I, Ni and Ga.

8. A process according to claim 6 in which said heteropoly acid is a heteropoly acid of molybdic acid wherein the hetero-atom is one selected from the group consisting of P, As, S:, Ge, Ti, Ce, Th, Mn, Ni, Te, I, Co, Cr, Fe and Ga.

9. A process according to claim 6 in which said heteropoly acid is a mixed coordination heteropoly acid selected from the group consisting of tungstomolybdophosphoric acid, tungstovanadophosphoric acid, vanadomolybdophosphoric acid, tungstomolybdosilicic acid, tungstovanadosilicic acid and vanadomolybdosilicic acid.

10. A process according to claim 7 in which said heteropoly acid of tungstic acid contains P or Si as a hetero-atom.

11. A process according to claim 8 in which said heteropoly acid of molybdic acid contains P or Si as hetero-atom.

12. A process according to claim 9 in which the mixed coordination heteropoly acid is an acid selected from the group consisting of $H_4PMoW_{11}O_{40}$, $H_4PReW_{11}O_{40}$, $H_4PVMo_{11}O_{40}$, $H_5PV_2Mo_{10}O_{40}$ and $H_3PMo_6W_6O_{40}$.

13. A process according to claim 1 in which said catalyst is 12-tungstophosphoric acid, 12-tungstosilicic acid or 12-molybdophosphoric acid.

14. A process according to claim 1 in which said condensation reaction is carried out in the presence of said catalyst and at least one dehydrating agent selected from the group consisting of phosphorus oxides and polyphosphoric acids.

15. A process according to claim 14 in which said dehydrating agent is added to the reaction system when the conversion of the aromatic sulfonic acid has reached about 40 to about 95%.

16. A process according to claim 15 in which said conversion is about 70 to about 95%.

17. A process according to claim 14 in which said dehydrating agent is diphosphorus pentoxide, diphosphorus trioxide, pyrophosphoric acid, tripolyphosphoric acid, metaphosphoric acid, trimetaphosphoric acid or tetrametaphosphoric acid.

18. A process according to claim 17 in which said dehydrating agent is added to the reaction system in an amount of about 0.01 to about 1.0 mole, calculated as phosphoric acid, per mole of the aromatic sulfonic acid or sulfuric acid.

* * * * *